US008119396B2

(12) United States Patent
Eloit et al.

(10) Patent No.: US 8,119,396 B2
(45) Date of Patent: Feb. 21, 2012

(54) RECOMBINANT ADENOVIRAL VECTORS AND APPLICATIONS THEREOF

(75) Inventors: Marc Eloit, Saint Maur des Fosses (FR); Bernard Klonjkowski, Joinville le Pont (FR)

(73) Assignees: Institut National de la Recherche Agronomique (INRA), Paris (FR); Ecole Nationale Veterinaire d'Alfort, Maisons Alfort (FR)

( * ) Notice: Subject to any disclaimer, the term of this patent is extended or adjusted under 35 U.S.C. 154(b) by 34 days.

(21) Appl. No.: 10/530,712

(22) PCT Filed: Oct. 8, 2003

(86) PCT No.: PCT/FR03/02964
§ 371 (c)(1),
(2), (4) Date: Nov. 8, 2005

(87) PCT Pub. No.: WO2004/033696
PCT Pub. Date: Apr. 22, 2004

(65) Prior Publication Data
US 2006/0233756 A1 Oct. 19, 2006

(30) Foreign Application Priority Data
Oct. 8, 2002 (FR) .................................... 02 12472

(51) Int. Cl.
*C12N 15/861* (2006.01)
*C12P 21/04* (2006.01)
*A01N 63/00* (2006.01)

(52) U.S. Cl. .................... 435/320.1; 435/70.1; 424/93.1
(58) Field of Classification Search ........................ None
See application file for complete search history.

(56) References Cited

U.S. PATENT DOCUMENTS
6,294,377 B1 * 9/2001 Haddada et al. ........... 435/320.1

FOREIGN PATENT DOCUMENTS
WO 01/42481 6/2001

OTHER PUBLICATIONS

BLAST Alignment results of SEQ ID No. 12, 1-360, with human adenovirus 5 genome, generated by the Examiner and printed on Apr. 12, 2009, 5 pages.*
Schmid, S. et al., "Bipartite Structure and Functional Independence of Adenovirus Type 5 Packaging Elements", 1997, J. Virol., vol. 71: pp. 3375-3384.*
Claire Soudais et al.: "Characterization of cis-Acting Sequences Involved in Canine Adenovirus Packaging", MolecularTherapy: The Journal of American Society of Gene Therapy, vol. 3, No. 4, pp. 631-640, Apr. 2001. XP-002242928.
M. Eloit et al.: "Isogenic adenoviruses type 5 expressing or not expressing the E1A gene: efficiency as virus vectors in the vaccination of permissive and non-permissive species", Journal of General Virology, vol. 76, No. 7, pp. 1583-1589, Jul. 1, 1995. XP 002028963.
Maria Grable et al.: "cis and trans Requirements for the Selective Packaging of Adenovirus Type 5 DNA", Journal of Virology, vol. 66, No. 2, pp. 723-731, Feb. 1992. XP 002012398.
Ramon Alemany et al.: "Complementation of helper-dependent adenoviral vectors: size effects and titer fluctuations", Journal of Virological Methods, vol. 68, No. 2, pp. 147-159, Nov. 1997. XP-001070256.
Mark D. Morrison et al.: "Generation of E3-Deleted Canine Adenoviruses Expressing Canine Parvovirus Capsid by Homologous Recombination in Bacteria", Virology, vol. 293, No. 1, pp. 23-30, Feb. 1, 2002. XP-002206291.
Eric J. Kremer et al.: "Canine Adenovirus Vectors: an Alternative for Adenovirus-Mediated Gene Transfer", Journal of Virology, vol. 74, No. 1, pp. 505-512, Jan. 2000. XP-002167110.

* cited by examiner

*Primary Examiner* — Michael Burkhart
(74) *Attorney, Agent, or Firm* — Oblon, Spivak, McClelland, Maier & Neustadt, L.L.P.

(57) ABSTRACT

Recombinant adenoviruses or pseudoviruses having a deletion of all or part of the region of the adenovirus genome corresponding to nucleotides 311 to 499 in canine adenovirus type 2 (GeneBank J04368). Therapeutic methods of using the recombinant adenovirus or pseudovirus.

14 Claims, 7 Drawing Sheets

RECOMBINANT ADENOVIRAL VECTORS AND APPLICATIONS THEREOF

The present invention relates to novel recombinant adenoviruses and the method for preparing them, as well as to their uses as expression and gene transfer vectors for vaccinatory purposes or for therapeutic purposes such as the treatment of cancer.

Adenoviruses are naked viruses which possess a linear double-stranded DNA genome of about 30-40 kbp in size, flanked by short inverted repeat sequences (ITRs).

The genome of the adenovirus is organized in early transcription units (E1 to E4) and a late unit (MLTU) which is composed of five transcript families (L1 to L5) whose expression is separated by the initiation of the replication of the viral DNA.

The early phase begins, two hours after infection, with the transcription and sequential expression of the regions E1A then E4, almost simultaneously E3 and E1B, then E2A and finally E2B. The immediate early region E1A encodes transactivators of other early genes of the adenovirus (E1B, E2, E3 and E4) as well as of cellular genes. Replication of the viral DNA begins eight hours after infection. The late phase, which commences twelve hours after infection, is characterized by abolition of the synthesis of the cellular proteins in favor of the late viral proteins, which enter into the structural composition of the adenoviral particle and participate in the assembly of the virion and its release while modifying the structural integrity of the infected cell.

The adenoviruses are particularly attractive for developing viral vectors due to their characteristics and the amount of knowledge which is available with regard to their genetic organization and their biology.

Different construction strategies have been considered depending on whether the aim is to obtain a replicating virus, which is able to multiply in the host (human or animal), or a nonreplicating virus which is unable to multiply in the host.

Constructing a nonreplicating vector involves deleting a region which is essential for viral replication. The resulting viruses, which are unable to replicate and consequently to produce infectious particles in cells which are permissible for infection by the corresponding wild-type virus, are produced in modified cell lines which are able to supply the products of the deleted genes in trans.

A strategy which is commonly used consists in inserting a heterologous gene into the left-hand part of the genome between the left ITR and the E1 region in place of the promoter and of the coding region of the E1A gene (partial E1 deletion) and, where appropriate, of the E1B gene (total deletion of the E1 region). The viruses from which E1A has been deleted are unable to replicate in cells which do not complement the E1A functions. However, they are able to express substantial quantities of exogenous protein in the infected cells.

A large number of human adenoviral vectors (Ad2 and Ad5) in which the E1 region and, where appropriate, the E3 region are deleted have been constructed, mainly for the purpose of human gene therapy. Mutations (E2 region) or additional deletions (E2 or E4 region) have been introduced for the purpose of improving these vectors.

Nonreplicating canine adenoviral vectors in which all the E1 region has been deleted have also been developed for human gene therapy applications [Klonjkowski et al., Human Gene Therapy, 8, 2103-2115, 1997, deletion of positions 411 to 2898 of Cav2; application WO 95/14101 and U.S. Pat. No. 5,837,531 in the name of Rhone Poulenc Rorer; Kremer et al., J. Virol., 74, 505-512, 2000, deletion of positions 412 to 2497 of Cav2).

These nonreplicating vectors have demonstrated good efficiency in transferring genes into a large number of tissues. However, they suffer from a certain number of disadvantages in particular for transferring genes into actively dividing cells such as tumor cells. In these cells, rapid abolition of the expression of the transferred gene is observed, with this abolition being linked to the loss of the extrachromosomal vector during the course of successive divisions.

Constructing a replicating vector involves the necessity of not eliminating any sequence in the viral genome which is essential for its replication and for the production of infectious viral particles in the host (productive viral cycle). Only a small number of heterologous sequence insertion sites which satisfy these requirements are at present known in adenoviruses.

Replicating vectors have been obtained by inserting heterologous genes into nonessential regions such as the E3 region and the right-hand part of the genome between the right ITR and the transcriptional regulation sequences of the E4 promoter. Replicating vectors have also been obtained by inserting a heterologous gene into the left-hand part of the genome between the left ITR and the E1 region provided that functional E1 genes are preserved. More precisely, insertion of a heterologous sequence between positions 455 and 917 of the human adenovirus (Ad5), which inactivates the E1A gene by deleting the promoter and a part of the coding region of E1A, is compensated by inserting a copy of this gene into the vector in an ectopic position (E1 oit et al., J. Gen. Virol., 76, 1583-1589, 1995).

Replicating vectors have been constructed in this way from human (E1 oit et. al., see above), bovine (Mittal et al., J. Gen. Virol., 76, 93-102, 1995), ovine (Xu et al., Virology, 230, 62-71, 1997), avian (Michou et al., J. Virol., 73, 1399-1410, 1999; Sheppard et al., Arch. Virol., 143, 915-930, 1998), canine (Cav2; international application WO 98/00166 and U.S. Pat. No. 6,090,393, in the name of Rhone Merieux; international application WO 91/11525 and U.S. Pat. No. 5,616,326 in the name of Glasgow University, Morrison et al., Virology, 293, 26-30, 2002) and porcine (Reddy et al., J. Gen. Virol., 80, 563-570, 1999; Tuboly et al., J. Gen. Virol., 82, 183-190, 2001) adeno-viruses.

These replicating adenoviruses have been mainly developed for vaccinatory applications. In a general manner, they have demonstrated a high level of efficacy in connection with inducing immune responses, both as far as the antibody response and the CTL response are concerned (for a review, see E1 oit, Virologie [Virology], 2, 109-120, 1998 and Klonjkowski et al., in "Adenoviruses: basic biology to gene therapy", pp. 163-173, P. Seth, Ed., R. G. Landes Company, Austin Tex., USA).

However, these replicating vectors suffer from some drawbacks:
- they pose problems of biosafety linked to the risk of these replicating viruses spreading,
- the substantial quantity of the viral particles which is produced by the infected cells leads to a powerful immune response being induced against the vector and limits the efficacy of repeat injections,
- neutralization by the maternal antibodies of the vaccinatory antigen which is released from cells which have been destroyed by the infection decreases the efficacy of these replicating vectors in the young animal.

It is apparent that no recombinant adenovirus which makes it possible to efficiently transduce cells, in particular dividing cells such as tumor cells, without involving risks of dissemination into the environment is currently available.

In choosing type 2 canine adenovirus (Cav2) as an experimental model, the inventors sought to determine whether it was possible to identify new insertion sites which made it possible to obtain replicating recombinant adenoviruses.

Thus, they observed that deleting a small proportion of the beginning of the region located between the end of the left ITR and the beginning of the sequence encoding E1A did not affect the ability of the adenoviruses to replicate their genome and to multiply in a permissive host, the site of this deletion can therefore constitute a novel site for inserting heterologous genes.

In addition, the inventors observed that, surprisingly, other deletions in the same region made it possible to obtain adenoviruses which were able to replicate their genome in a permissive host but which were unable to multiply. These adenoviruses will be designated "pseudoreplicating adenoviruses" below.

In that which follows, the positions of the different regions of the adenoviral genome are defined by reference to the positions of the corresponding regions (that is to say, containing elements having a similar function) of the genome of the type 2 canine adenovirus in the GenBank J04368 sequence.

Thus, the region located between the end of the left ITR and the beginning of the sequence encoding E1A corresponds to that located between position 311 and position 499 in the GenBank J04368 genomic sequence of type 2 canine adenovirus.

The present invention relates to a recombinant adenovirus which can be obtained from a replicating adenovirus by deleting all or part of the region of the genome of said replicating adenovirus which corresponds to that located between positions 311 and 499 in the genome of type 2 canine adenovirus (GenBank J04368), with said deletion comprising all or part of the region of the genome of the original replicating adenovirus corresponding to that located between positions 311 and 401 in the genome of type 2 canine adenovirus.

According to a first embodiment of a recombinant adenovirus according to the invention, the deleted portion consists of all or part of the region of the genome of the original replicating adenovirus which corresponds to that located between positions 311 and 319 in the genome of type 2 canine adenovirus; this deletion makes it possible to obtain a replicating recombinant adenovirus which is able to multiply in a host which is permissive to infection with an original wild-type adenovirus (productive viral cycle).

According to a second embodiment of a recombinant adenovirus according to the invention, the deleted portion comprises all or part of the region of the genome of the original replicating adenovirus which corresponds to that located between positions 318 and 401 in the genome of type 2 canine adenovirus; this deletion advantageously makes it possible to obtain pseudoreplicating adenoviruses, that is to say adenoviruses which are able to replicate but unable to produce infectious viral particles and therefore unable to multiply (abortive cycle) in a host which is permissive to infection with the original wild-type adenovirus.

Obtaining pseudoreplicating adenoviruses according to the invention involves, in particular, eliminating all or part of the putative encapsidation signals of the 5'-TTTA/G-3' $A_X$, $A_{XI}$, and $A_{XII}$ type (respectively located in positions 341-344, 377-380 and 388-391 in the GenBank J04368 Cav2 sequence).

The portion which is deleted in these pseudoreplicating adenoviruses can additionally comprise:

all or part of the region of the genome of the original replicating adenovirus corresponding to that located between positions 311 and 319 in the genome of type 2 canine adenovirus; and/or all or part of the region of the genome of the original replicating adenovirus corresponding to that located between positions 400 and 439 in the genome of type 2 canine adenovirus; this deletion eliminates, in particular, the TATA box of the E1A promoter (located in position 409 in the GenBank J04368 Cav2 sequence); and/or all or part of the region of the genome of the original replicating adenovirus corresponding to that located between positions 438 and 499 in the genome of type 2 canine adenovirus; this deletion eliminates, in particular, the E1A transcription initiation site (located in position 439 in the GenBank J04368 Cav2 sequence).

In all these cases, the (replicating or pseudoreplicating) recombinant adenoviruses according to the invention retain the left ITR sequences which are essential for replication and for activating transcription (4 repeated GGTCA motifs located between positions 62 and 99 in the Cav2 genome) as well as the 5'TTGN$_8$CG-3' type $A_I$ (positions 207-219) and 5'-TTTA/G-3' type $A_{II}$ to $A_{IX}$ encapsidation signals (respectively located at positions 197-200 ($A_{II}$), 206-209 ($A_{III}$), 213-216, 228-232 ($A_{IV}$) 239-242 ($A_V$), 250-253 ($A_{VI}$), 258-261 ($A_{VII}$), 272-275 ($A_{VIII}$) and 306-309 ($A_{IX}$) in the Cav2 genome). They also retain all of the E1A coding sequence as well as regions of the E1 gene located downstream thereof (E1A polyadenylation signal and E1B region).

According to a preferred embodiment of a recombinant adenovirus according to the invention, it additionally comprises at least one heterologous sequence of interest inserted in its genome.

In order to construct a recombinant adenovirus in accordance with this embodiment, said heterologous sequence will, in the case of a replicating adenovirus, be inserted into the region of the genome corresponding to that located between positions 311 and 319 in the genome of type 2 canine adenovirus.

In the case of a pseudoreplicating adenovirus, said heterologous sequence can also be inserted into this region or at any other site in the region of the genome corresponding to that located between positions 311 and 499 in the genome of type 2 canine adenovirus. The insertion into this region can be effected in place of the deleted portion or in the vicinity thereof.

A heterologous sequence can also be inserted into any one of the sites which are normally used for this purpose for constructing replicating adenoviruses. The insertion can, for example, be effected in the E3 region or in the region located between the E4 region and the right ITR, as described in U.S. Pat. No. 6,090,393, or in the 3' portion of the right ITR, as described in U.S. Pat. No. 5,616,326.

A "heterologous sequence" is understood as meaning any sequence other than that contained between positions 311 and 499 in the genome of said wild-type adenovirus.

The following may be mentioned as nonlimiting examples:
genes encoding a vaccinal antigen, for example the gag or env genes of the feline immunodeficiency virus (FIV), the S, M or N protein of the feline coronavirus, a canine or feline parvovirus capsid protein, the G glycoprotein of the rabies virus or the Leptospira sp. Hap-1 protein, etc.

corrective genes which can be used in gene therapy, for example that for erythropoietin (Epo), for vascular endothelium growth factor (VEGF), for neurotrophin 3 (NT-3) or for atrial natriuretic factor (ANF), etc.;

genes which can be used for treating cancer, for example that for IL-2, that for IFNγ, etc.

Recombinant adenoviruses according to the invention can, in particular, be derived from mammalian adenoviruses and, in particular, canine adenoviruses, in particular type 2 canine adenoviruses.

The recombinant adenoviruses according to the present invention can be prepared using customary techniques which are per se well known to the skilled person (cf., for example, GRAHAM and PREVEC (Manipulation of Adeno-virus Vectors, Methods Mol. Biol., 7, 109-128, 1991), in particular using techniques comprising: (i) using standard techniques of double homologous recombination to generate recombinant genomes in E. coli and (ii) transfecting the resulting recombinant genomes into suitable cell lines which enable said genomes to be amplified and encapsidated in infectious viral particles.

It will be possible, for example, to use homologous recombination techniques in E. coli, such as those described by CHARTIER et al., (J. Virol., 70, 7, 4805-4840, 1996) and in U.S. Pat. No. 6,110,735 in the name of TRANSGENE or else those described by CROUZET et al., (Proc. Nat. Acad. Sci. USA, 94, 1414-1419, 1997). These methods are based on an intermolecular homologous recombination between a "recipient" DNA molecule containing the complete genome of an adenovirus and a "donor" DNA molecule comprising a heterologous sequence to be inserted into said genome flanked by sequences which are homologous with those of the region of the adenoviral genome where it is desired to effect the insertion. The recipient molecule is linearized by cleaving at a restriction site which is unique in the genome of the adenovirus and which is located at the insertion site. Selection of the recombinant genomes is then based on circularization of the recipient molecule.

These methods therefore suffer from the drawback of only being able to insert said heterologous sequence into a region comprising a restriction site which is unique in the genome of the adenovirus.

The inventors have now developed a method for inserting a heterologous sequence into an adenovirus, which method does not require linearizing the genome of the adenovirus by cleaving at the insertion site.

This method differs from that described by CHARTIER et al. in that:
1) the heterologous DNA fragment (donor molecule) to be inserted into the genome of the adenovirus (recipient molecule) comprises a selection marker which makes it possible to isolate the recombinant plasmids on the basis of their double resistance to both ampicillin and kanamycin, and
2) said fragment is cotransformed with a recipient molecule which is either in circular form or in a form which has been linearized by cleaving at a restriction site which is located outside the insertion site.

Consequently, the present invention also relates to a method for preparing a recombinant adenovirus by means of intermolecular homologous recombination in a prokaryotic cell, characterized in that it comprises the following steps:

α) introducing, into said prokaryotic cell: (i) a plasmid comprising the genome of an adenovirus and a first selection gene; and (ii) a previously linearized DNA fragment which comprises a heterologous sequence to be inserted into said genome flanked by sequences which are homologous to those flanking the site of said plasmid where the insertion is to be effected and which includes a second selection gene which differs from the first; and β) culturing said prokaryotic cell under selective conditions in order to make it possible to generate and select cells which harbor recombinant plasmids which are expressing the first and second selection genes, and γ) isolating the genome of said recombinant adenovirus from selected cells.

"Selective conditions" are understood as meaning culture conditions under which the first and second selection agents (for example antibiotics) are present at concentrations which do not allow untransformed cells to multiply but which allow cotransformed cells to multiply.

According to a first embodiment of the invention, the plasmid which is used in α) is in circular form.

According to a second embodiment of the invention, the plasmid used in step α) has been previously linearized by cleaving at a restriction site which is located outside the insertion site.

According to another advantageous embodiment of the invention, the first and/or second selection gene is a gene for resistance to an antibiotic, for example a gene for resistance to ampicillin or kanamycin.

According to another embodiment of the invention, the second selection gene is flanked by 2 identical or different restriction sites which are absent from the genome of the adenovirus used in step α); this selection gene can therefore be excised from the sequence of the genome of the recombinant adenovirus by digesting at these sites.

Advantageously, the method according to the invention comprises, after preparing the recombinant genome as described in steps α) to γ) above, an additional step of transfecting the recombinant genome into a suitable cell line which enables said genome to be amplified and encapsidated in infectious viral particles.

In order to prepare recombinant adenoviruses according to the invention, it is possible to use cell lines which are known per se to the skilled person (cf., for example, GRAHAM and PREVEC, see above) and which are expressing the E1 region of the adenovirus and, where appropriate, the E4 region of the adenovirus when this latter has been impaired by inserting a heterologous sequence of interest. Cell lines which can be used, and which may be mentioned, in particular, are human cell lines such as the 293 cell line (GRAHAM et al., J. Gen. Virol., 36, 59-74, 1977) and canine cell lines such as the DK/E1-28 cell line (KLONJKOWSKI et al., Human Gene Therapy, see above). Advantageously, it will be possible to use a new cell line which has been constructed by the inventors and which is modified by inserting a fragment consisting of the sequence corresponding to that which extends from position 439 to position 3595 in the genome of the (GenBank J04368) type 2 canine adenovirus; this cell line does not contain the sequences which are located upstream of position 439 and which are present in the above-mentioned cell lines of the prior art.

Said cell line is preferably of canine origin.

The invention additionally relates to plasmids and nucleic acid molecules which can be used for preparing the genome of a recombinant adenovirus according to the invention, in particular a canine adenovirus, and to said recombinant genomes which an be obtained by the methods as defined above.

The invention relates, in particular, to the following nucleic acid molecules and plasmids:

any nucleic acid molecule which is selected from the group consisting of:
  a) a nucleic acid molecule which represents the genome of a recombinant adenovirus according to the invention as defined above;
  b) a nucleic acid molecule which consists of a fragment of the molecule a) above and which comprises between 10 and 1000 bp, preferably at least 300 bp, of the sequence of the original replicating adenovirus located upstream of the deleted portion and between 10 and 5000 bp, preferably between 10 and 1000 bp, preferably at least 300 bp, of the sequence of the original replicating adenovirus located downstream of the deleted portion; such a molecule can additionally comprise all or part of a heterologous sequence which is inserted in place of the deleted portion or in proximity thereto.

any nucleic acid vector, in particular any plasmid, which contains an a) or b) nucleic acid molecule as defined above.

The invention also relates to the recombinant adenoviruses according to the invention for use as drugs.

The invention relates, in particular, to the use of the adenoviruses according to the invention for preparing immunogenic or vaccinatory compositions or drugs which are intended for gene therapy or for treating cancer as well as for producing recombinant proteins.

Said drug or said composition is preferably intended to be administered to a wild or domestic carnivore, in particular a cat, dog or fox or else a human.

The recombinant adenoviruses according to the invention are particularly well suited for therapeutic uses, for example vaccinatory therapeutic uses, in man and animals. This is because, contrary to the nonreplicating recombinant adenoviruses, whose genome is present at low copy numbers per cell and rapidly eliminated from actively dividing cells, the replicating or pseudoreplicating recombinant adenoviruses according to the invention multiply significantly in the nucleus of the transduced cells, making it possible to efficiently transduce both quiescent cells and actively dividing cells such as tumor cells. In addition, the pseudoreplicating adenoviruses according to the invention, which do not produce any infectious particle, exhibit a high degree of biosafety and also make it possible to induce a strong immune response in connection with repeat injections.

Recombinant adenoviruses according to the invention, for example those derived from the canine adenovirus, have applications for vaccinating and treating cancer in domestic or wild carnivores, in particular cats, dogs and foxes. In addition, due to a host tropism of their own, these canine adenoviruses can be used in human gene therapy for targeting tissues which are different from those which can be transduced by the human vectors, for example cells of the central nervous system.

The present invention will be better understood with the help of the remainder of the description which follows and which refers to nonlimiting examples which illustrate the construction and preparation of a recombinant adenovirus according to the invention and its use for expressing genes of interest, in particular for vaccination.

EXAMPLE 1

Constructing the Adenoviruses CAV 311-319, CAV 311-439 and CAV 311-401

1) Constructing the Recombinant Plasmids

The following plasmids were constructed using the standard protocols for preparing, cloning and analyzing DNA such as those described in *Current Protocols in Molecular Biology (Frederick M. AUSUBEL, 2000, Wiley and Son Inc., Library of Congress, USA)* a) Plasmid pCav2 Containing the Complete Sequence of the Genome of Type 2 Canine Adenovirus (Cav2)

This plasmid is constructed by homologous recombination in *E. coli*, in analogy with the method for preparing human adenoviruses, as described in CHARTIER et al., see above.

Figure 1:
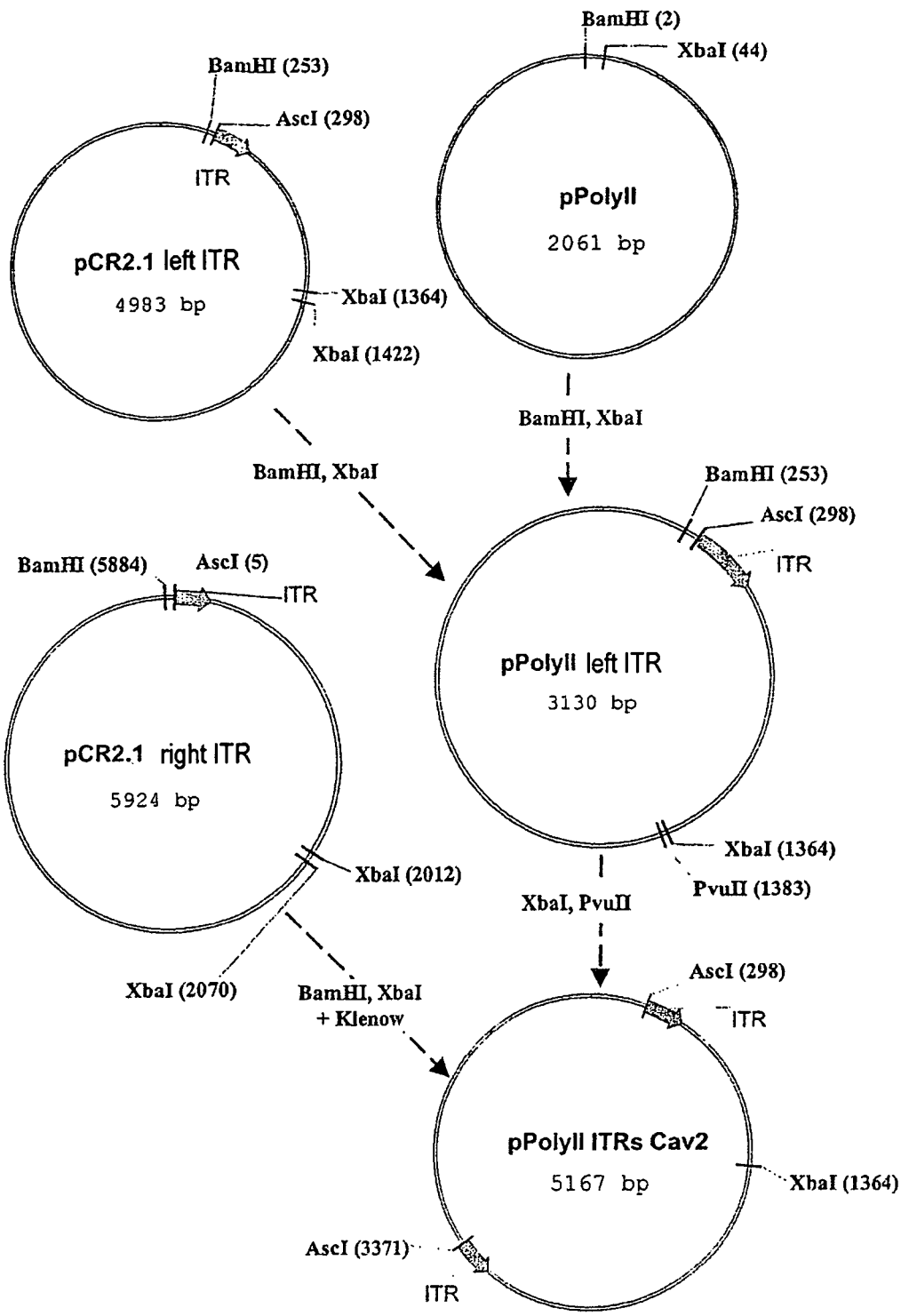
FIG. 1 shows main steps involved in constructing Plasmid pCav2 that contains the complete sequence of the genome of type 2 canine adenovirus (Cav2).

The main steps involved in constructing this plasmid are shown in FIG. 1.

More precisely, the left and right ends of the genome of the Manhattan strain of Cav2, corresponding to the sequences at positions 1 to 1060 (fragment A) and 29323-31323 (fragment B) are amplified separately by PCR from the genomic DNA of the Cav2 Manhattan strain (APPEL et al., Am. J. Vet. Res., 34, 543-550, 1973) using the following primers:

Fragment A

```
5'-TTGGCGCGCCCATCATCAATAATATACAGGAC-  (SEQ ID NO: 1)
3'

5'-GCTCTAGACCTGCCCAAACATTTAACC-3'     (SEQ ID NO: 2)
```

Fragment B

```
5'-TTGGCGCGCCCATCATCAATAATATACAGGAC-  (SEQ ID NO: 1)
3'

5'-GCTCTAGAGGGTGATTATTAACAACGTC-3'    (SEQ ID NO: 3)
```

The resulting fragments A and B are separately cloned into the plasmid pCR2.1 (TA Cloning System, INVITROGEN) in order to give, respectively, the plasmids pCR2.1/left ITR and pCR2.1/right ITR. The plasmid pCR2.1/left ITR is digested with BamHI and XbaI and the 1111 bp fragment which is thus generated is cloned between the BamHI and XbaI sites of the plasmid pPolyII Amp$^R$ (GenBank M18128, LATHE et al., Gene, 57, 193-201, 1987) in order to give the plasmid designated pPolyII/left ITR. The plasmid pCR2.1/right ITR is cleaved with BamHI, treated with Klenow polymerase and then cleaved with XbaI; the 2052 bp fragment which is thus generated is cloned between the XbaI and PvuII sites of the plasmid pPolyII/left ITR in order to give the plasmid pPolyII-.ITRs.Cav2. This plasmid contains the left and right ends of the genome of the Cav2 Manhattan strain which are cloned in the form of a 3073 bp AscI-AscI fragment comprising an XbaI site in position 1066 of said fragment, making it possible to linearize the plasmid at the DNA insertion site.

The genomic DNA of the Cav2 Manhattan strain and the pPolyII.ITRs.Cav2 DNA, which is linearized at the XbaI site, are cotransformed into the E. coli strain BJ5183 recBC sbcBC (HANAHAN et al., J. Mol. Biol., 166, 557-580, 1983). A 33425 bp recombinant plasmid, designated pCav2, is isolated from the colonies which are resistant to ampicillin.

Plasmid pCav2 contains the complete genome of Cav2 (Manhattan strain) cloned in the form of a 31331 bp fragment flanked by two AscI sites which are unique in this plasmid, with these sites being absent from the Cav2 genome (Manhattan and Toronto strains) as well as from that of the ovine adenovirus strain OAV.

b) Shuttle Plasmids b$_1$) pShuttle/311-439/CMVeGFP

This 6111 bp plasmid is derived from the plasmid pBluescript KS (STRATAGENE) by inserting Cav2 sequences upstream and downstream of the 312-438 deletion (UpRecSeq 1-311 and DownRecSeq 439-1060) at either end of a cassette for expressing the reporter gene GFP.

This plasmid is constructed in accordance with the following steps:

1) a fragment C, corresponding to the sequence at positions 1 to 311 (UpRecSeq) of Cav2, is amplified by PCR using the primers:

5'-TTGGCGCCCATCATCAATAATATACAGGAC-3' (SEQ ID NO: 1)

5'-CCGACGTCGACCATAAACTTTGACATTAGCCG-3'. (SEQ ID NO: 4)

The PCR amplification product is cloned into the plasmid pCR2.1 in order to give the plasmid pCR2.1/UpRecSeq (1-311).

2) a fragment D, corresponding to the sequence at positions 439 to 1060 (DownRecSeq) of Cav2, is amplified by PCR using the primers:

5'-GCTCTAGAGCGAAGATCTCCAACAGCAATACACTCTTG-3' (SEQ ID NO: 5)

5'-GCTCTAGACCTGCCCAAACATTTAACC-3'. (SEQ ID NO: 2)

The PCR amplification product is cloned into the plasmid pCR2.1 in order to give the plasmid pCR2.1/DownRecSeq (439-1060).

3) A fragment E of approximately 2050 bp, containing the early cytomegalovirus promoter, an intron, the eGFP (enhanced Green Fluorescent Protein) coding sequence and a polyadenylation signal, is obtained in accordance with the following steps:

The plasmid pEGFP-1 (CLONTECH) is cleaved with BamHI, treated with Klenow polymerase and then digested with NotI; the 741 bp fragment which is thus obtained is cloned between the XhoI (previously repaired by treating with the Klenow polymerase) and NotI sites of the plasmid pCI (PROMEGA) in order to give the plasmid pCMVeGFP.

The pCMVeGFP plasmid is then cleaved with BglII, treated with Klenow polymerase and then digested with BamHI in order to generate a 2050 bp fragment (fragment E).

4) The fragment E is inserted between the SmaI and BamHI sites of the plasmid pBLUESCRIPT KS in order to give the plasmid pKS/CMVeGFP. The plasmid pCR2.1/UpRecSeq (1-311) is cleaved with KpnI and SalI and the 371 bp fragment thus obtained (fragment C) is cloned between the KpnI and SalI sites of the plasmid pKS/CMVeGFP in order to give the plasmid pKS/CMVeGFP-C. The plasmid pCR2.1/DownRecSeq (439-1060) is cleaved with XbaI and the 650 bp fragment thus obtained (fragment D) is inserted into the XbaI site of the plasmid pKS/CMVeGFP-C in order to give the plasmid designated pShuttle 311-439/CMVeGFP.

b$_2$) pShuttle 311-401/CMVeGFP

The shuttle plasmid pShuttle 311-401/CMVeGFP is constructed from the plasmid pShuttle 311-439/CMVeGFP in accordance with the following steps:

The sequence 401-1060 (DownRecSeq) is amplified by PCR using the primers:

5'-GATAAGGATCACGCGGCCTTAAATTCTCAG-3' (SEQ ID NO: 6)

5'-GCTCTAGACCTGCCCAAACATTTAACC-3'. (SEQ ID NO: 2)

The PCR amplification product is cloned in the plasmid pCR2.1 in order to give the plasmid pCR2.1/DownRecSeq (401-1060).

This plasmid pCR2.1/DownRecSeq (401-1060) is digested with EcoRI and then treated with Klenow polymerase and the 401-1060 fragment thus obtained is substituted for the 439-1060 fragment of the plasmid pShuttle 311-439/CMVeGFP, which has been previously digested with XbaI and then treated with Klenow polymerase, in order to give the plasmid pshuttle 311-401/CMVeGFP.

b$_3$) pshuttle 311-319/CMVeGFP

The shuttle plasmid pShuttle 311-319/CMVeGFP is constructed from the plasmid pShuttle 311-439/CMVeGFP in accordance with the following steps:

The 319-1060 sequence (DownRecSeq) is amplified by PCR using the primers:

5'-GATAAGGATCAACAGAAACACTCTGTTCTCTG-3' (SEQ ID NO: 7)

5'-GCTCTAGACCTGCCCAAACATTTAACC-3'. (SEQ ID NO: 2)

The PCR amplification product is cloned into the plasmid pCR2.1 in order to give the plasmid pCR2.1/DownRecSeq (319-1060).

This plasmid pCR2.1/DownRecSeq (319-1060) is digested with EcoRI and then treated with Klenow polymerase and the 319-1060 fragment thus obtained is substituted for the 439-1060 fragment of the plasmid pshuttle 311-439/CMVeGFP, which has been previously digested with XbaI and then treated with Klenow polymerase, in order to give the plasmid pshuttle 311-319/CMVeGFP.

b$_4$) Shuttle Plasmid pShuttle 311-439/CMVeGFP/Kana

This 7027 bp plasmid, which is derived from the plasmid pShuttle 311-439/CMVeGFP by cloning, into the PmeI site, a cassette for expressing a gene for resistance to kanamycin in the opposite orientation to that of the cassette for the GFP, is obtained in accordance with the following steps:

The reading frame encoding the Kana gene is amplified by PCR from the plasmid pET-29a(+) (NOVAGEN) using the primers:

```
5'-AGCTTTGTTTAAACGGCGCGCCGGGATTTTGGT (SEQ ID NO: 8)
CATGAAC-3'

5'-CCGGCGCGCCGTTTAAACAAAGCTATCCGCTCA (SEQ ID NO: 9)
TGAA-3'.
```

The PCR amplification product is cloned into the plasmid pCR2.1 in order to give the plasmid pCR2.1-Kana/PmeI. The plasmid pCR2.1/Kana/PmeI is cleaved with EcoRI and treated with Klenow polymerase and the fragment of approximately 959 bp in size, containing the reading frame encoding the Kana gene, is inserted into the EcoRV site of the plasmid pshuttle 311-439/CMVeGFP in order to give the plasmid pshuttle 311-439/CMVeGFP/Kana.

Figure 2:
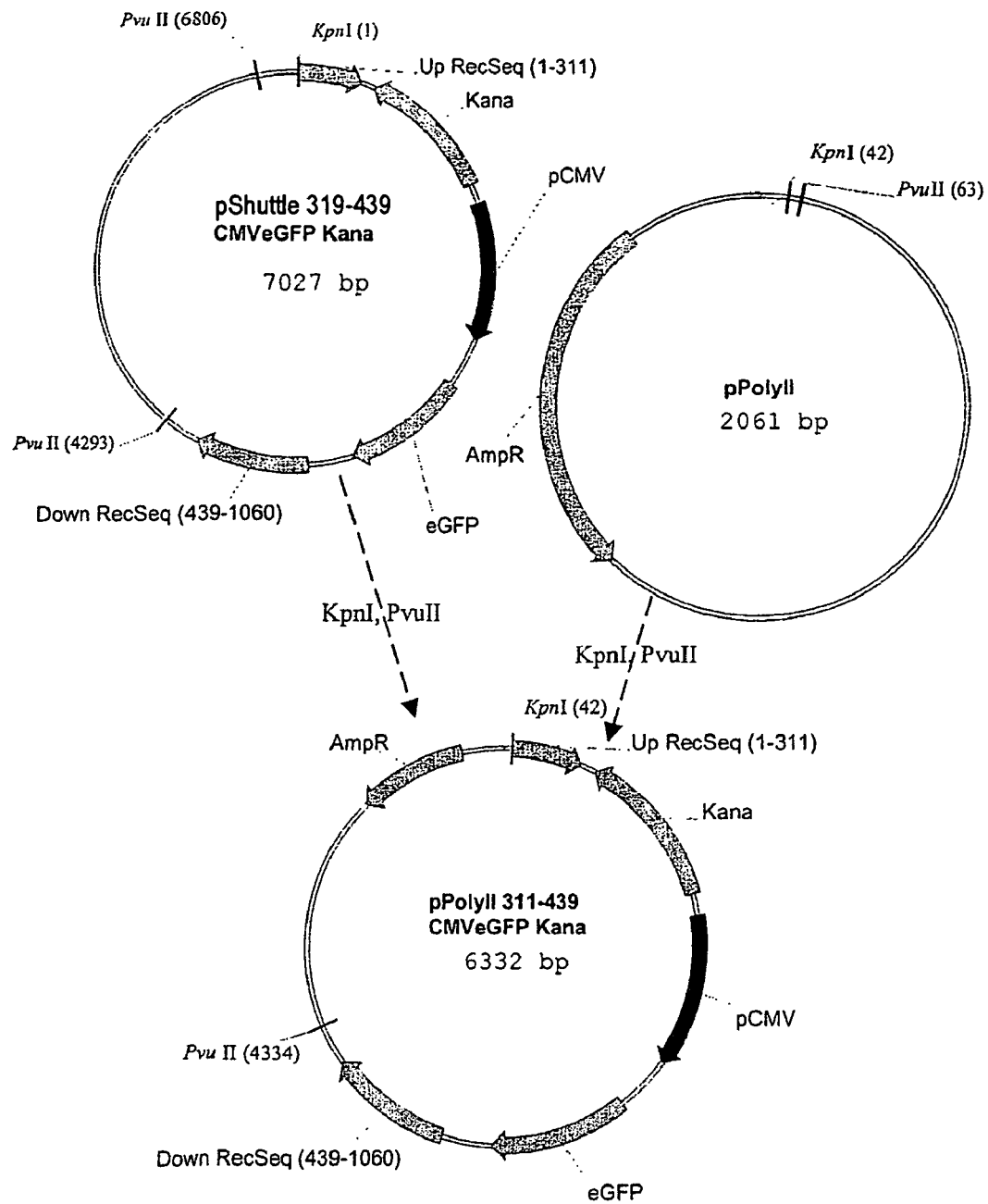
FIG. 2 depcits plasmid pShuttle 311-439/CMVeGFP/Kana.

This plasmid pShuttle 311-439/CMVeGFP/Kana, which is depicted in FIG. 2 and which contains a gene for resistance to an antibiotic cloned between the adenoviral sequences which are the target of the recombination, upstream of the heterologous sequence to be inserted, advantageously makes it possible to select the recombinants which are resistant to both ampicillin and kanamycin. In addition, the Kana gene, which is then excised from the recombinant plasmid by digesting at the 2 PmeI sites, is absent from the recombinant adenovirus sequence which is generated from this plasmid.

b$_4$) Shuttle Plasmid pPoly II 311-439/CMVeGFP/Kana (FIG. 2)

This 6332 bp plasmid is obtained by cloning the 4292 bp KpnI-PvuII fragment of pShuttle 311-439/CMVeGFP between the KpnI (position 42) and PvuII (position 63) sites of the plasmid pPoly II, as illustrated in FIG. 2.

c) Plasmid pCav 311-439/CMVeGFP

Figure 3:
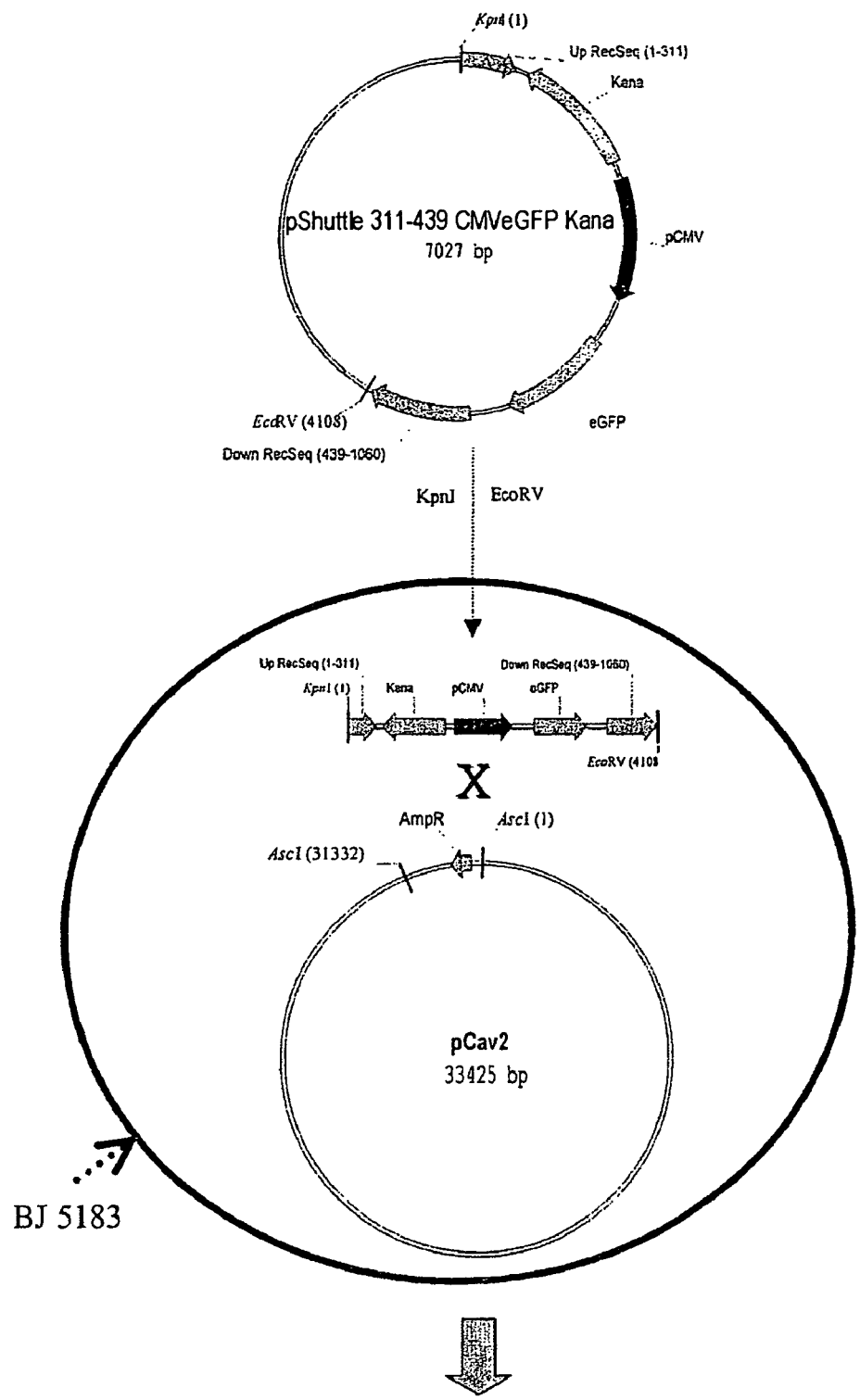
FIG. 3 shows $c_1$) recombination of pShuttle 311-439/CMVeGFP.Kana with plasmid pCav2 in circular form.
Figure 4:
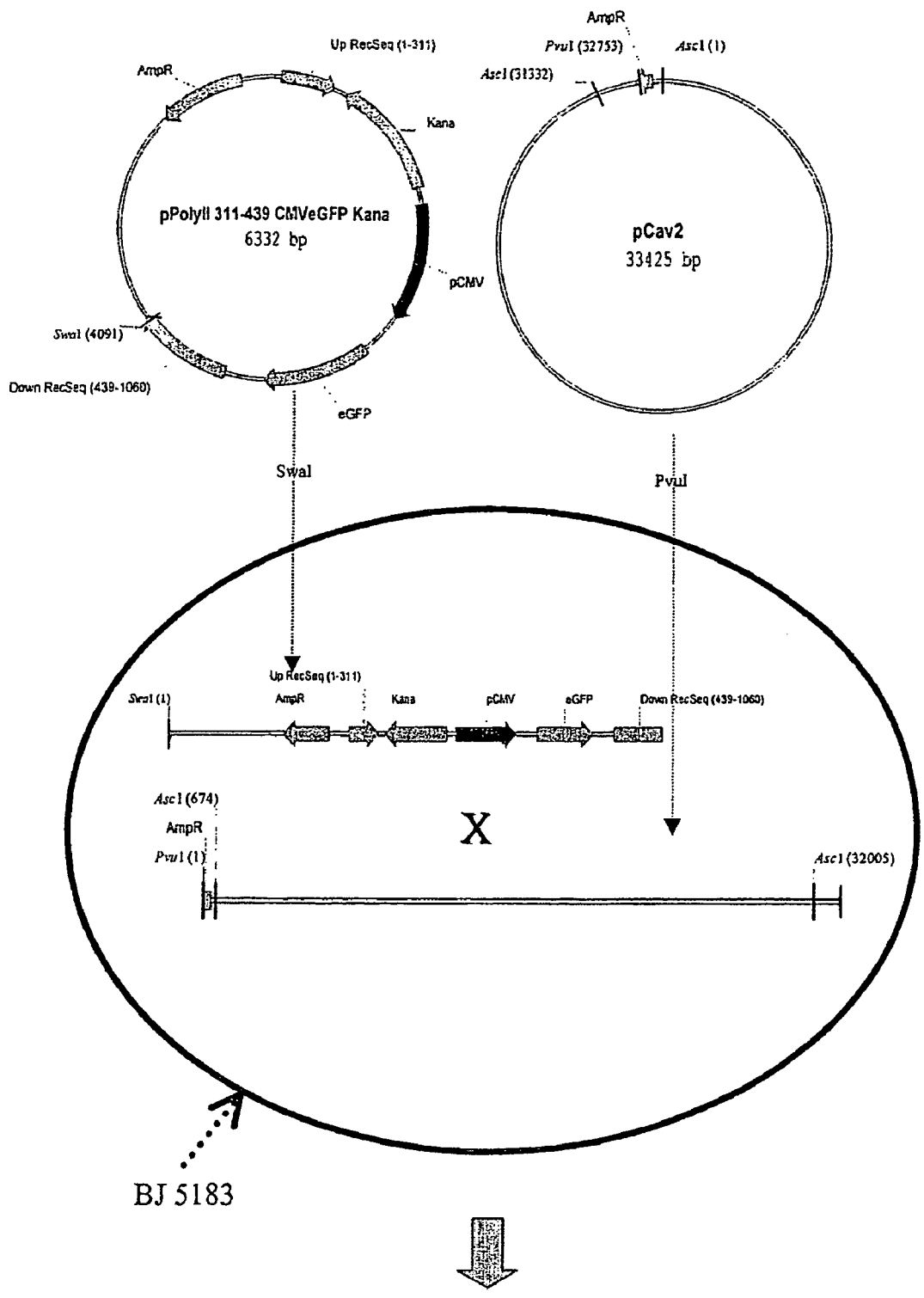
FIG. 4 shows $c_2$) recombination of pPoly II 311-439/CMVeGFP.Kana with the plasmid pCav2, which has been previously linearized outside the insertion site.

This plasmid is obtained by homologous recombination in the *E. coli* strain BJ5183 in accordance with the following 2 alternatives c1 and c2, which are respectively illustrated by FIGS. 3 and 4:

c$_1$) Recombination of pShuttle 311-439/CMVeGFP.Kana with Plasmid pCav2 in Circular form (FIG. 3)

1) the donor molecule, containing the upstream (UpRecSeq 1-311) and downstream (DownRecSeq 439-1060) recombination sequences and the CMVeGFP and Kana cassettes, is prepared from the plasmid pshuttle 311-439/CMVeGFP.Kana by digesting with the restriction enzymes KpnI and EcoRV,
2) the fragment obtained in 1) and the plasmid pCav2 (Amp$^R$) in circular form are cotransformed into the *E. coli* strain BJ5183, and
3) the recombinant plasmids are isolated on the basis of the criterion of resistance to both ampicillin and kanamycin. The sequence of one of them, pCav 311-439/CMVeGFP/Kana, is confirmed by enzymic restriction and by sequencing.
4) The Kana cassette is then excised by digesting with the restriction enzyme PmeI so as to obtain the plasmid pCav 311-439/CMVeGFP, which contains the Cav2 genome from which the 312-438 sequence has been deleted and replaced with a cassette for expressing GFP.

c$_2$) Recombination of pPoly II 311-439/CMVeGFP.Kana With the Plasmid pCav2, which has been Previously Linearized Outside the Insertion Site (FIG. 4)

1) the donor molecule is prepared from the pPoly II 311-439/CMVeGFP.Kana plasmid by digesting with the restriction enzyme SwaI,
2) the plasmid pCav2 is linearized by cleaving at the PvuI site,
3) the fragment obtained in 1) and the linearized pCav2 plasmid obtained in 2) are cotransformed into the *E. coli* strain BJ5183, and
4) the recombinant plasmids are isolated on the basis of the criterion of resistance to both ampicillin and kanamycin. The sequence of one of them, pcav 311-439/CMVeGFP-.Kana, is confirmed by enzymic restriction and by sequencing.
5) The Kana cassette is then excised by digesting with the restriction enzyme PmeI so as to obtain the plasmid pcav 311-439/CMVeGFP, which contains the Cav2 genome from which the sequence at positions 312-438 has been deleted, with this sequence being replaced by a cassette for expressing GFP.

d) Plasmid pCav 311-401/CMVeGFP

The plasmid pshuttle 311-401/CMVeGFP is digested with KpnI and SwaI and the 3167 bp fragment thus obtained, and the plasmid pcav 311-439/CMVeGFP which is linearized at the PmeI site, are cotransformed into the *E. coli* strain BJ5185. The recombinant plasmid pcav 311-401 CMVeGFP, which is generated by homologous recombination, is selected on the basis of the criterion of resistance to both ampicillin and kanamycin.

e) Plasmid pCav 311-319/CMVeGFP

The plasmid pshuttle 311-319/CMVeGFP is digested with KpnI and SwaI and the 3249 bp fragment which is thus obtained, and the plasmid pCav 311-439 CMVeGFP which has been linearized at the PmeI site, are cotransformed into the *E. coli* strain BJ5185. The recombinant plasmid pcav 311-319 CMVeGFP, which is generated by homologous recombination, is selected on the basis of the criterion of resistance to both ampicillin and kanamycin.

2) Producing Recombinant Viruses

The plasmids pcav 311-439/CMVeGFP, pcav 311-401/CMVeGFP or pcav 311-319/CMVeGFP are digested with the restriction enzyme AscI in order to excise the sequences of the recombinant adenovirus genome. The excised adenoviral genome is then transformed into the canine cell line DK/E1-28, which constitutively expresses the Cav2 E1 region (KLONJKOWSKI et al., Human Gene Therapy, see above), in the presence of lipofectamine (GIBCO) in accordance with the customary techniques which are well known per se to the skilled person (cf., for example, GRAHAM and PREVEC, see above). When a cytopathic effect is observed, the virus is harvested from the transfected cells, then amplified in the same DK/E1-28 cell line and purified by centrifugation through a cesium chloride gradient using a standard protocol, such as described, for example, in GRAHAM and PREVEC, see above.

The genomic sequence of the viruses Cav 311-439/CMVeGFP, Cav 311-401/CMVeGFP and Cav 311-319/CMVeGFP is confirmed by enzymic restriction and by partial sequencing of the viral DNA, which is extracted from the infected DK/E1-28 cells and prepared in accordance with the HIRT technique (J. Mol. Biol., 26, 365-369, 1967). The recombinant Cav virus preparations are titrated by limiting dilution on 96-well plates in accordance with the method of SPEARMAN and KÄRBER (*Virology Methods Manual*, Brian W J Mahy and Hillar O Kangro, 1996, Academic Press, Harcourt Brace & Company). The TCID$_{50}$/ml titer which is obtained by this method is equivalent to the pfu/ml titer which is obtained by the method plaques on DK cells, in accordance with the protocol described in KLONJKOWSKI et al., see above.

The following results are obtained:
the isolated viruses Cav 311-439/CMVeGFP, Cav 311-401/CMVeGFP and Cav 311-319/CMVeGFP have a restriction profile and a sequence which is in accordance with those which are expected,
the purified viruses Cav 311-439/CMVeGFP, Cav 311-401/CMVeGFP and Cav 311-319/CMVeGFP have a titer of approximately $10^{9.2}$ pfu/ml.

EXAMPLE 2

Characterizing the Recombinant Virus Cav 311-439

1) Analyzing the Efficiency of Transduction and the Cytopathic Effect of Cav 311-439 CMVeGFP in Feline and Canine Cells Canine (DK/E1-28 and DK) or feline (CRFK) cell lines are infected with the virus Cav 311-439 CMVeGFP at a multiplicity of infection of 10 pfu/cell. Uninfected cells and cells which are infected with the wild-type Cav virus (Cav2) are used as controls.

At 3 and 5 days after the infection, the presence of a cytopathic effect (EPE) is analyzed by observing infected cells in an optical microscope. In addition, the expression of the transgene by the Cav 311-439 CMVeGFP virus in the infected cells is confirmed by detecting the GFP by fluorescence microscopy.

The results of this experiment are presented in tables I and II below:

TABLE I

| Virus | DK | DK/E1-28 | CRFK |
|---|---|---|---|
| Cav 311-439 CMVeGFP | − | ++ | − |
| Cav | + | ++ | − |
| Control | − | − | − |

TABLE II

| Cells infected with Cav 311-439.CMVeGFP | ECP | GFP |
|---|---|---|
| DK | − | + |
| DK/E1-28 | ++ | ++ |

These results show that:
a high level of expression of the transgene by the Cav 311-439 CMVeGFP virus is observed in the infected cells, and
no cytopathic effect is observed in the unmodified canine cells (DK cells) or feline cells which are infected with this virus Cav 311-439 CMVeGFP; a substantial cytopathic effect is only observed in the canine cells which are infected with this Cav 311-439 CMVeGFP virus and which are expressing the E1 region,
in the controls, a substantial cytopathic effect is observed in the canine cells (DK and DK/E1-28) which are infected with the wild-type Cav (Cav2) and no cytopathic effect is observed in the feline cells which are infected with Cav2.

The results of these experiments demonstrate that the Cav 311-439 viruses are able to very efficiently transduce the cells without inducing any cytopathic effect in the canine cells which are permissive for replication of the wild-type canine adenoviruses, or in the feline cells.

2) Analyzing the Replication of Cav 311-439 CMVeGFP in the Feline and Canine Cells Canine (DK/E1-28 and DK) or feline (CRFK) cell lines are infected with the virus Cav 311-439 CMVeGFP at a multiplicity of infection of 10 pfu/cell. Uninfected cells and cells infected with the wild-type Cav virus are used as controls.

At 2, 24, 48 and 72 hours after the infection, the cells are harvested and centrifuged. The intracellular viral DNA is prepared using the HIRT technique (J. Mol. Biol., 26, 365-369, 1967), digested with the enzyme EcoRI and then visualized on an agarose gel following electrophoretic migration.

Figure 5:
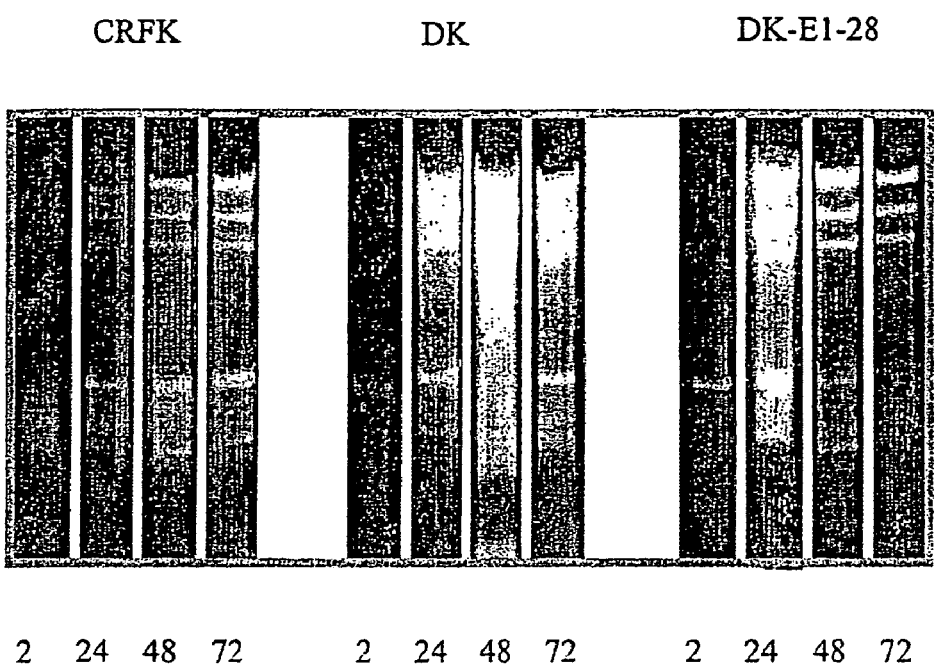
FIG. 5 shows viral DNA extracted from feline (CRFK) or canine (DK, DK/E1-28) cells at different times after infection (2, 24, 48 and 72 hours) with the adenovirus Cav 311-439.CMVeGFP is digested with EcoRI and analyzed on an agarose gel. The cell line DK/E1-28, which expresses the E1 region of the adenovirus, is used as a positive control for replication.

The results are depicted in FIG. 5:

Legend to FIG. 5: viral DNA extracted from feline (CRFK) or canine (DK, DK/E1-28) cells at different times after infection (2, 24, 48 and 72 hours) with the adenovirus Cav 311-439.CMVeGFP is digested with EcoRI and analyzed on an agarose gel. The cell line DK/E1-28, which expresses the E1 region of the adenovirus, is used as a positive control for replication.

These results show that:
the Cav 311-439 CMVeGFP virus replicates its genome in the tested canine and feline cell lines,
the level of replication is greater in the canine cells than in the feline cells,
the peak of replication is reached at 24 hours in the DK/E1-28 cells and at 48 hours in the DK cells, probably because of the cellular expression of the E1 region in the DK/E1-28 cells.

By comparison, in the control cells infected with the wild-type Cav virus, a similar quantity of genomic DNA is observed in the 3 cell lines.

The results of this experiment demonstrate that the 311-439 deletion does not affect the replication of the canine adenovirus: the vectors which carry this deletion (Cav 311-439 CMVeGFP) behave like the wild-type adenoviruses as far as the replication of their genome in canine or feline cells is concerned.

3) Analyzing the Production of Viral Particles in the Canine Cells Infected with the Virus Cav 311-439.CMVeGFP DK canine cell lines are infected with the vector Cav 311-439 CMVeGFP at a multiplicity of infection of, respectively, 0.1, 1 and 10 pfu/cell. Uninfected cells and cells infected with the wild-type Cav virus are used as controls.

The infected cells are harvested at 2 hours and 6 days after the infection, and lysed by several cycles of freezing and thawing. The cell lysate is titrated by the abovementioned technique of limiting dilutions.

The quantity of virus present in the cells, expressed in pfu/ml, is shown in table III below.

TABLE III

| Virus | Time | 0.1 pfu/cell | 1 pfu/cell | 10 pfu/cell |
|---|---|---|---|---|
| Cav 311-439 | D0 | $<10^{1.8}$ | $10^{2.4}$ | $10^3$ |
|  | D6 | $<10^{1.8}$ | $10^3$ | $10^{2.8}$ |
| Cav | D0 | $10^2$ | $10^3$ | $10^{4.4}$ |
|  | D6 | $10^{7.6}$ | $10^{6.8}$ | $10^{6.8}$ |

These results show that the Cav 311-439 virus does not produce infectious viral particles in canine cells, such as the DK cells, which are not expressing the E1 region: the Cav 311-439 viral cycle is abortive in the canine cells.

4) Vaccinating Conventional Cats with the Cav 311-439 Virus

Groups of cats are inoculated intramuscularly with the following doses of Cav 311-439:
group 1 (n=2): 9.6 $10^7$ pfu
group 2 (n=2): 9.6 $10^6$ pfu
group 3 (n=2): control.

On D14, D21 and D31, the serum anti-eGFP antibodies are titrated by ELISA.

Figure 6:
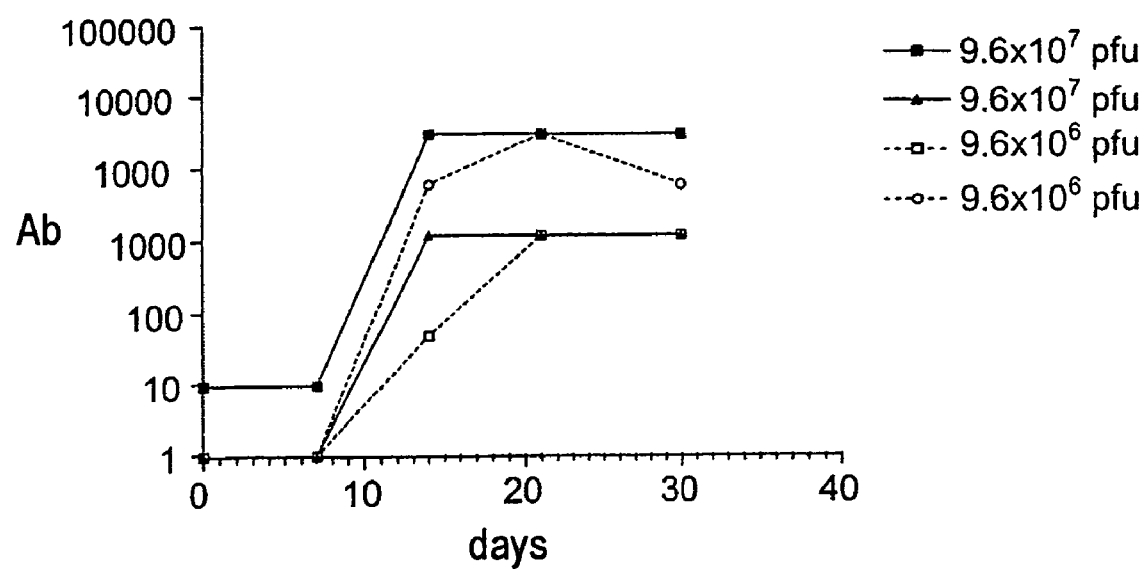
FIG. 6 depicts serum anti-eGFP antibody (Ab) titers in the cat on days D7, D14, D21 and D31 after the inoculation of different doses of the Cav 311-439.CMVeGFP virus: -■- 9.6 $10^7$ pfu/ml (pfu: plaque forming units), -▲- 9.6 $10^7$ pfu/ml, •••□••• 9.6 $10^6$ pfu/ml, •••○••• 9.6 $10^6$ pfu/ml.

The results are depicted in FIG. 6.

Legend to FIG. 6: serum anti-eGFP antibody (Ab) titers in the cat on days D7, D14, D21 and D31 after the inoculation of different doses of the Cav 311-439.CMVeGFP virus: -■- 9.6 $10^7$ pfu/ml (pfu: plaque forming units), -▲- 9.6 $10^7$ pfu/ml, •••□••• 9.6 $10^6$ pfu/ml, •••○••• 9.6 $10^6$ pfu/ml.

These results show that a single injection of Cav 311-439 induces a (humoral) immune response in the cat which is specific for the gene of interest.

EXAMPLE 3

Constructing a Canine-Derived Cell Line Which Constitutively Expresses the Cav2 E1 Region A new cell line expressing the E1 region is constructed from the DK cell line (immortalized line of dog kidney cells; ATCC CRL 6247) by means of the following steps:

The sequence at positions 439 to 3595 of Cav2 (Manhattan strain) is amplified by PCR using the following primers:

```
5'-CGGCCGACTCTTGAGTGCGCAGCGAGA-3'    (SEQ ID NO: 10)

5'-GGCGCGCCGAGAGACAACGCTGGACACGG-    (SEQ ID NO: 11)
3'.
```

The PCR amplification product is cloned into the plasmid pCR2.1 to give the plasmid pCR2.1/E1.

The plasmid pTRE (CLONTECH) is digested with BamHI, treated with Klenow polymerase and recircularized in order to give the plasmid pTRE/dl BamHI.

The plasmid pCR2.1/E1 is digested with EcoRI and the 3187 bp fragment which is thus obtained is cloned into the EcoRI site of the plasmid pTRE/dl BamHI in order to give the plasmid pTRE E1 Cav2.

This plasmid pTRE E1 Cav2 contains the coding sequence for the E1A protein under the control of a minimum CMV promoter and response elements of the Tet operon (Tet-Responsive Element or TRE), the sequences coding for the E1B proteins (133R and 438R; SHIBATA et al., Virology, 172, 460-467, 1989) under the control of their own promoter and the endogenous polyadenylation signals for these sequences.

Using pTRE E1 Cav2 as the starting material, a cell line expressing the E1 region is obtained in an analogous manner to that used for obtaining the DK/E1-28 cell line (KLONJKOWSKI et al., see above).

More precisely, the DK cells are cotransfected with the pTRE E1 Cav2 plasmid, which is linearized at the AatII site, and with the plasmid pTK-Hyg (CLONTECH), which is linearized at the AseI site. Clones are selected in the presence of hygromycin (150 μg/ml) and then analyzed by Southern blotting, Northern blotting, RT-PCR and Western blotting. 4 clones which expressed the E1 region (E1A and E1B), and which were able to efficiently produce the deleted vectors according to the invention, were isolated.

EXAMPLE 4

Immunizing Mice With the Cav 311-319 Virus

Mice which had been divided into three groups were inoculated intramuscularly with a 108 pfu dose of the following viruses:

Group 1 (n=4): Cav 311-319 eGFP

Group 2 (n=4): Cav 311-319 CONTROL

Group 3 (n=1): uninoculated control.

The Cav 311-319 CONTROL virus is isogenic with the Cav 311-319 eGFP virus apart from the heterologous gene which is inserted (a heterologous gene encoding a protein which does not have any antigenic relationship with GFP is inserted in place of the gene encoding GFP).

On D7, the serum anti-eGFP antibodies which were produced by the inoculated mice were titrated by Elisa.

Figure 7:
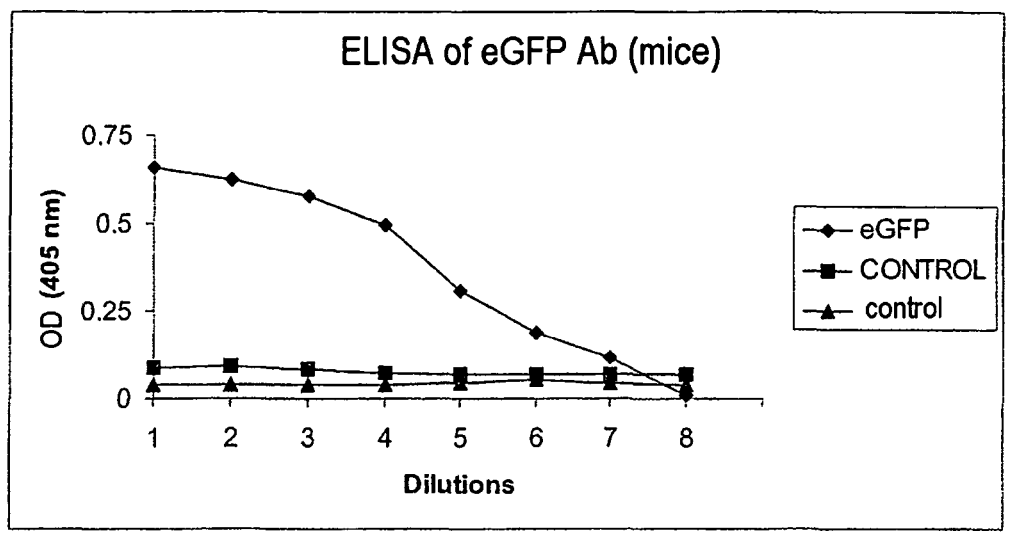
FIG. 7 shows OD at 405 nm for different dilutions (from 1 to 8, respectively, $\frac{1}{5}$, $\frac{1}{15}$, $\frac{1}{45}$, $\frac{1}{135}$, $\frac{1}{405}$, $\frac{1}{1215}$, $\frac{1}{3645}$ and $\frac{1}{10935}$) of the mouse sera of the following groups: eGFP (♦), CONTROL (■) and control (▲).

The results are depicted in FIG. 7.

Legend to FIG. 7: OD at 405 nm for different dilutions (from 1 to 8, respectively, 1/5, 1/15, 1/45, 1/135, 1/405, 1/1215, 1/3645 and 1/10935) of the mouse sera of the following groups: eGFP (♦), CONTROL (■) and control (▲).

These results show that a single injection of Cav 311-319 induces a (humoral) immune response in the mouse which is specific for the heterologous gene which is inserted in this adenovirus.

The invention claimed is:

1. A recombinant canine type 2 adenovirus that can replicate and produce infectious viral particles that contains a deletion in the segment between positions 311 and 319 in SEQ ID NO: 12; said adenovirus retaining all of the E1A coding sequence as well as regions of the E1 gene located downstream thereof, said regions including the E1A polyadenylation signal and the E1B region.

2. The recombinant adenovirus of claim 1, which comprises the E1, E2 and E4 coding regions and the right and left ITRs of replicating canine type 2 adenovirus.

3. The recombinant adenovirus of claim 1, which comprises the E1, E2 and E4 coding regions, the right and left ITRs and the E3 coding region of replicating canine type 2 adenovirus.

4. The recombinant adenovirus of claim 1, wherein the deleted portion comprises all or part of the region of the genome of replicating canine type 2 adenovirus corresponding to positions 318 and 401 of SEQ ID NO: 12.

5. The recombinant adenovirus of claim 1, wherein the deleted portion further comprises:

all or part of the region of the genome of replicating canine type 2 adenovirus corresponding to that located between positions 400 and 439 of SEQ ID NO: 12; and/or all or part of the region of the genome of replicating canine type 2 adenovirus corresponding to that located between positions 438 and 499 of SEQ ID NO: 12.

6. The recombinant adenovirus of claim 1, which further comprises a heterologous polynucleotide sequence of interest inserted in its genome.

7. The recombinant adenovirus of claim 6, wherein said heterologous sequence is inserted in the region of the genome corresponding to that located between positions 311 and 319 SEQ ID NO: 12.

8. A pharmaceutical composition comprising the recombinant adenovirus of claim 1.

9. A method for making a recombinant protein comprising introducing the recombinant adenovirus of claim 1 into a host cell, said recombinant adenovirus further comprising in its genome a heterologous polynucleotide, wherein the recombinant adenovirus is introduced into the host cell for a time and under conditions suitable for expression of a recombinant protein from said genome, and recovering said recombinant protein.

10. A nucleic acid molecule:
comprising the genome of the recombinant adenovirus of claim 1.

11. A plasmid comprising the nucleic acid molecule of claim 10.

12. A method for stimulating an immune response specific to a peptide or a protein comprising:
administering to a subject in need thereof the recombinant adenovirus of claim 1, wherein the recombinant adenovirus comprises in its genome a heterologous polynucleotide encoding the specific peptide or protein.

13. The method of claim 12, which comprises stimulating the production of antibodies to the specific peptide or protein.

14. The method of claim 12, wherein the heterologous polynucleotide encoding the specific peptide or protein is introduced between positions 311 and 319 in the genome of the recombinant adenovirus.

* * * * *

SEQUENCE LISTING

```
<160> NUMBER OF SEQ ID NOS: 12

<210> SEQ ID NO 1
<211> LENGTH: 32
<212> TYPE: DNA
<213> ORGANISM: Artificial Sequence
<220> FEATURE:
<223> OTHER INFORMATION: Synthetic DNA

<400> SEQUENCE: 1
ttggcgcgcc catcatcaat aatatacagg ac                              32

<210> SEQ ID NO 2
<211> LENGTH: 27
<212> TYPE: DNA
<213> ORGANISM: Artificial Sequence
```

```
<220> FEATURE:
<223> OTHER INFORMATION: Synthetic DNA

<400> SEQUENCE: 2
gctctagacc tgcccaaaca tttaacc                                    27

<210> SEQ ID NO 3
<211> LENGTH: 28
<212> TYPE: DNA
<213> ORGANISM: Artificial Sequence
<220> FEATURE:
<223> OTHER INFORMATION: Synthetic DNA

<400> SEQUENCE: 3
gctctagagg gtgattatta acaacgtc                                   28

<210> SEQ ID NO 4
<211> LENGTH: 32
<212> TYPE: DNA
<213> ORGANISM: Artificial Sequence
<220> FEATURE:
<223> OTHER INFORMATION: Synthetic DNA

<400> SEQUENCE: 4
ccgacgtcga ccataaactt tgacattagc cg                              32

<210> SEQ ID NO 5
<211> LENGTH: 38
<212> TYPE: DNA
<213> ORGANISM: Artificial Sequence
<220> FEATURE:
<223> OTHER INFORMATION: Synthetic DNA

<400> SEQUENCE: 5
gctctagagc gaagatctcc aacagcaata cactcttg                        38

<210> SEQ ID NO 6
<211> LENGTH: 30
<212> TYPE: DNA
<213> ORGANISM: Artificial Sequence
<220> FEATURE:
<223> OTHER INFORMATION: Synthetic DNA

<400> SEQUENCE: 6
gataaggatc acgcggcctt aaattctcag                                 30

<210> SEQ ID NO 7
<211> LENGTH: 32
<212> TYPE: DNA
<213> ORGANISM: Artificial Sequence
<220> FEATURE:
<223> OTHER INFORMATION: Synthetic DNA

<400> SEQUENCE: 7
gataaggatc aacagaaaca ctctgttctc tg                              32

<210> SEQ ID NO 8
<211> LENGTH: 40
<212> TYPE: DNA
<213> ORGANISM: Artificial Sequence
<220> FEATURE:
<223> OTHER INFORMATION: Synthetic DNA

<400> SEQUENCE: 8
agctttgttt aaacggcgcg ccgggatttt ggtcatgaac                      40
```

```
<210> SEQ ID NO 9
<211> LENGTH: 37
<212> TYPE: DNA
<213> ORGANISM: Artificial Sequence
<220> FEATURE:
<223> OTHER INFORMATION: Synthetic DNA

<400> SEQUENCE: 9
ccggcgcgcc gtttaaacaa agctatccgc tcatgaa                                    37

<210> SEQ ID NO 10
<211> LENGTH: 27
<212> TYPE: DNA
<213> ORGANISM: Artificial Sequence
<220> FEATURE:
<223> OTHER INFORMATION: Synthetic DNA

<400> SEQUENCE: 10
cggccgactc ttgagtgcgc agcgaga                                               27

<210> SEQ ID NO 11
<211> LENGTH: 29
<212> TYPE: DNA
<213> ORGANISM: Artificial Sequence
<220> FEATURE:
<223> OTHER INFORMATION: Synthetic DNA

<400> SEQUENCE: 11
ggcgcgccga gagacaacgc tggacacgg                                             29

<210> SEQ ID NO 12
<211> LENGTH: 3609
<212> TYPE: DNA
<213> ORGANISM: Canine adenovirus type 2
<220> FEATURE:
<221> NAME/KEY: misc_signal
<222> LOCATION: (62)..(99)
<223> OTHER INFORMATION: Four repeated GGTCA motifs; left ITR sequences
<220> FEATURE:
<221> NAME/KEY: misc_signal
<222> LOCATION: (197)..(200)
<223> OTHER INFORMATION: 5'TTTA/G-3' type AII encapsidation signal
<220> FEATURE:
<221> NAME/KEY: misc_signal
<222> LOCATION: (206)..(209)
<223> OTHER INFORMATION: 5'TTTA/G-3' type AIII encapsidation signal
<220> FEATURE:
<221> NAME/KEY: misc_signal
<222> LOCATION: (207)..(219)
<223> OTHER INFORMATION: 5'TTGN8CG-3' type AI encapsidation signal
<220> FEATURE:
<221> NAME/KEY: misc_signal
<222> LOCATION: (228)..(212)
<223> OTHER INFORMATION: 5'TTTA/G-3' type AIV encapsidation signal
<220> FEATURE:
<221> NAME/KEY: misc_signal
<222> LOCATION: (239)..(242)
<223> OTHER INFORMATION: 5'-TTTA/G-3' type AV encapsidation signal
<220> FEATURE:
<221> NAME/KEY: misc_signal
<222> LOCATION: (250)..(253)
<223> OTHER INFORMATION: 5'-TTTA/G-3' type AVI encapsidation signal
<220> FEATURE:
<221> NAME/KEY: misc_signal
<222> LOCATION: (258)..(261)
<223> OTHER INFORMATION: 5'-TTTA/G-3' type AVII encapsidation signal
<220> FEATURE:
<221> NAME/KEY: misc_signal
<222> LOCATION: (272)..(275)
<223> OTHER INFORMATION: 5'-TTTA/G-3' type AVIII encapsidation signal
<220> FEATURE:
<221> NAME/KEY: misc_signal
<222> LOCATION: (306)..(309)
<223> OTHER INFORMATION: 5'-TTTA/G-3' type AIX encapsidation signal
```

```
<220> FEATURE:
<221> NAME/KEY: misc_signal
<222> LOCATION: (341)..(344)
<223> OTHER INFORMATION: 5'-TTTA/G-3' type AX encapsidation signal
<220> FEATURE:
<221> NAME/KEY: misc_signal
<222> LOCATION: (377)..(380)
<223> OTHER INFORMATION: 5'-TTTA/G-3' type AXI encapsidation signal
<220> FEATURE:
<221> NAME/KEY: misc_signal
<222> LOCATION: (388)..(391)
<223> OTHER INFORMATION: 5'-TTTA/G-3' type AXII encapsidation signal
<220> FEATURE:
<221> NAME/KEY: TATA_signal
<222> LOCATION: (409)..(415)
<223> OTHER INFORMATION: TATA box of the E1A promoter
<220> FEATURE:
<221> NAME/KEY: misc_feature
<222> LOCATION: (439)..(439)
<223> OTHER INFORMATION: E1A transcription initiation site

<400> SEQUENCE: 12
catcatcaat aatatacagg acaaagaggt gtggcttaaa tttgggtgtt gcaaggggcg      60
gggtcatggg acggtcaggt tcaggtcacg ccctggtcag ggtgttccca cgggaatgtc     120
cagtgacgtc aaaggcgtgg ttttacgaca gggcgagttc cgcggacttt ggccggcgc     180 cccgggtttt tgggcgttta ttgattttgc ggtttagcgg gtggtgcttt taccactgtt     240
tgcggaagat ttagttgttt atggagctgg ttttggtgcc agttcctcca cggctaatgt     300
caaagtttat gtcaatataa cagaaacact ctgttctctg tttacagcac cccacccggt     360 ggttttttcgc cacgcctttg ggttaatttt atttccctat acgcggcctt aaattctcag     420
tgcagacgaa agaggactac tcttgagtgc gcagcgagaa gagttttctc ttcgctgtgt     480
ctcatatatt ttctgaaaaa tgaaatatac tattgtgccg gcgccgcgca atctccatga     540
ttatgtttta gagctactgg aagagtggca gccggactgc cttgactgtg agtattctca     600
tggcagcccc tcgccgccta ctctgcacga tcttttttgat gttgagctgg agacttctca     660 cagcccttt gtgggcctgt gtgattcctg tgcggaggct gacactgatt cgagtgcgag     720
cactgaggct gattctgggt ttagtccttt atccactccg ccggtttcac ctattccacc     780
gcatcccacc tctcctgcta gcatttctga cgacatgttg ctgtgcttag aggaaatgcc     840 caccttgat gacgaggacg aggttcgaag cgcggcgacc acctttgagc ggtgggaaaa     900
cacttttgac ccccatgtgg gtcctatttt tggctgtttg cgctgtgctt tttatcaaga     960
gcaggatgat aatgcacttt gtgggctttg ctatctaaag gcccttgccg aaggtaagtt    1020
ttaatttaaa tgtttgggca ggtaaatgt ttgggcaggt taaatgtttt aggtgtgtat    1080
tgatttttaa ttttgctttt tagtgccttt tgctatgcct gtacgttcag aacccgcttc    1140
ggctggagct gaggaggaag atgatgaagt tatttttgtg tctgccaaac ctgggggcag    1200
aaagaggtca gcagctactc cctgtgagcc agatggggtc agcaaacgcc cttgcgtgcc    1260
agagcctgag caaacagaac ctttggattt gtctttgaag ccacgcccga actaatctcc    1320
ttgagcacaa agcaataaag taatcttgtt taacaagttt gcctacattt gtggttttac    1380
ggggcggggc gaggagtata taatgccaaa agccagtgcc tgcttcatta agcttttaga    1440
ctgagctaag agcaggtagt atggacccta ttaagatttg tgaaaactac cttacttta    1500 gagctataat tagggaagt actttgtcgc ctggattttt taggcggtgg tgttttcctg    1560
ccttggctga tgtggtgggc aatatagtgg aacaggagga aggcaggttt tggcaaattt    1620
tacctgaaaa ccacgctttt tggggtcttt tgcgcagggg ctttactgtt gcttctttta    1680
ctgaaattat tacagcagct cagctggaaa atagaggtag acagttggcc ttttagcttt    1740
```

```
ttatatcatt tttgctacgc aactggcctt ctgactctgt agtgcctgaa gctgacagac    1800
ttgacctggt ctgtgcgccg gcatggagca gaatgagata tggagccaga ccgccaggtt    1860
aatcaacgac ctccaagatt ccgtgctcga ggagcagggg tccgcggaag aggaagagtg    1920
cgaagaagcg cttttagcag gggacagcga cgacccatta ttcgggtaga tgacttgcag    1980
ctgcccgacc ccctgtatgt tatgcaagct ttgcaacggg accacacttt agaaatgccc    2040
agagggcagg tagattttag ctggattgag gctgaagaga ggcgggtagg tcccacagac    2100
gagtggtact ttgaggctgt gaagacttac aaagctaagc cgggagatga cttgcaaact    2160
ataatcaaaa actatgccaa gatttcctta gaatgtgggg ccgtgtatga aattaattct    2220
aagattaggg ttacggggc ttgctacatt attggtaatt gtgccgtgct taggcctaac     2280
ctgcctgctg gagaagcaat gtttgaggtt ttgaatgttg attttattcc ttctattggt    2340
tttatggaaa ggatagtgtt ttccaatgtt attttttgatt gcaggaccac cgcaactgta   2400
gtgtgttgca ttagtgaaag aaacaccttg tttcacaatt gtgttttttc tggccctcac    2460
atgttatgtt tggaccttag ggcggggcg gaggtgaggg gctgtcactt tgtggggcg      2520 gtgtgtgcgt tgcgtagcaa ggggctgtac agtattcgag tcaaaaatag cattttgaa     2580 aagtgtgctt ttggggtggt gaccgggtca aaggcttcta ttagccattg catgtttaag    2640
gattgtacct gctctattat gctgggggt cagggcacta ttgcccatag tcagtttatt     2700
gtaactactt ctgctgaggc ccccatgaac ctgcaactgt gcacttgcga gggtaatgga    2760
agtcatgtag ttccattggg gaatattcac tttgcttctc accgggaagc ttcgtggcct    2820
acgttttatg caaacaccctt ggttcgggtg cgcttgtata tgggccggcg ccggggagtt   2880
tttcacccca agcagtctac tttgtcaatg tgtgtaattg cagcccctcg gggggttgtg    2940
cagagaattt atttgtttgg tgtgtatgat gctacttgtg ccattatgca actgggcgag    3000
gcaggcaatg ctgctagtga aagactgtgt acttgcgggt tcagacacag cacccccttcc   3060 ctgcgggcca cctatgtaac tgacaccagg attgaccggg agctgaactc tcaagacacg    3120
gctgagttct ttagcagtga tgaagataat ttttaggtga gtagatgggc gtggtttggg    3180
ggagtataaa aggggcgcgg tacgtggctg tgtatttaca gccatggacc ctcaacagaa    3240
ggggcttgtg aacacgtgtt ttgtgactac gcgtattccg tcttgggcag gagcaagaca    3300
gaatgtcacc gggtcagatt tagaaggaaa gcccgtgccc tcagatgtgc tggaaagtgg    3360
acgcccgctt gcagcccgc gcatcagaac tttgtatgag gagcagcagc tgaacatgct     3420
tgcggtgaat gttcttttgg atgagctgaa gatccaggtg gctgccatgc aaaactctgt    3480
gactgctatt cagcgagaag taaatgatct aaagcaacga atcgcccgag attaatgtaa    3540
aaataaaatt tatttctttt ttgaatgata ataccgtgtc cagcgttgtc tgtctgtaat    3600
agttctatg                                                            3609
```